US011650145B2

(12) United States Patent
Fang

(10) Patent No.: US 11,650,145 B2
(45) Date of Patent: May 16, 2023

(54) HYPERSPECTRAL SENSING SYSTEM AND METHOD FOR QUALITATIVE ANALYSIS OF FLUIDS

(71) Applicant: SAFENET INTERNATIONAL LLC, Arlington Heights, IL (US)

(72) Inventor: Joseph Y. Fang, South Barrington, IL (US)

(73) Assignee: SAFENET INTERNATIONAL LLC, Arlington Heights, IL (US)

( * ) Notice: Subject to any disclaimer, the term of this patent is extended or adjusted under 35 U.S.C. 154(b) by 43 days.

(21) Appl. No.: 17/396,986

(22) Filed: Aug. 9, 2021

(65) Prior Publication Data

US 2023/0043807 A1    Feb. 9, 2023

(51) Int. Cl.
| | | |
|---|---|---|
| *G01N 21/31* | (2006.01) | |
| *G01N 21/94* | (2006.01) | |
| *G01N 33/28* | (2006.01) | |
| *G01J 3/28* | (2006.01) | |

(52) U.S. Cl.
CPC ............ *G01N 21/31* (2013.01); *G01J 3/2823* (2013.01); *G01N 21/94* (2013.01); *G01N 33/2888* (2013.01); *G01J 2003/283* (2013.01); *G01J 2003/2879* (2013.01)

(58) Field of Classification Search
CPC . G01J 2003/2826; G01J 3/2823; G01N 21/31
See application file for complete search history.

(56) References Cited

U.S. PATENT DOCUMENTS

2019/0323889 A1*  10/2019  Sano .................... G01J 3/28
2020/0271591 A1*   8/2020  Havener ............... G01N 21/94

OTHER PUBLICATIONS

Jakob Kilgus, "Application of a Novel Low-Cost Hyperspectral Imaging Setup Operating in the Mid-Infrared Region", Nov. 30, 2018 (Year: 2018).*
Perkin Elmer "The Lab Report, Episode 9: Analysis of Wear Metals in New and Used Oil", May 9, 2016 (Year: 2016).*

* cited by examiner

*Primary Examiner* — Maurice C Smith
(74) *Attorney, Agent, or Firm* — Bishop, Diehl & Lee, Ltd.

(57) ABSTRACT

A system and method using remote sensing instrument with hyper spectrum quantitatively measure metal dust elements in lubricating oil, which includes (no limited): Al, Cd, Cr, Cu, Fe, Pb, Mg, Mn, Mo, Ni, Ag, Sn, Ti, V, Zn, B (Boron, for Coolant), Ca (Calcium for water contaminant), and particle size, cone penetration, dropping point, steel mesh oil separation, moisture, PQ concentration, in few seconds. The instrument integrates near-field communication (NFC) Internet of Thing (IoT) Cloud computing, spectral matching and other data processing, and application software forming a system to easily operated and build a model enable self-learning to improve precision through collection accumulation. With the system, the instrument as FIG. 1 can provide comprehensive on-site analysis enable preventive maintenance of mission critical engine and rotating equipment. The characteristics of the system are easy to operate, get result quickly, and self-learning to improve precision.

20 Claims, 6 Drawing Sheets

System Functional Component Flowchart

Calibration and Expert System

Processing Procedures to Build Hyperspectral Model

Processing Procedures to Calculate Test Results

Hyperspectral Models Built by Various Application Scenarios

HYPERSPECTRAL SENSING SYSTEM AND METHOD FOR QUALITATIVE ANALYSIS OF FLUIDS

TECHNICAL FIELD OF INVENTION

The present invention is directed to systems and methods using remote hyper-spectrum scanning to quantitatively measure metal dust elements in fluids, such as lubricating oil, quickly and expertly. Measurement obtained may include, without limitation, particle size, cone penetration, dropping point, steel mesh oil separation, moisture, and PQ concentration.

BACKGROUND OF INVENTION

Lubricant (Oil and Grease) analysis can provide critical information (i.e., a healthy condition) about a system powered by an engine. Such periodic lubricant analysis is needed in numerous industries, including aircraft industry, automobile and truck industry, the energy sector, wind turbines, the marine sector, mining, construction and other heavy equipment users, agriculture industry, military and many other government entities. A key benefit of lubricant analysis is the ability to diagnosis early conditions contributing to engine failure. Recommending and implementing preventive maintenance in response to the analysis helps avoid downtime and/or big repairs, which in turn leads to a productivity increase from increasing the uptime of running machines and vehicles.

There are various approaches to implementing a lubricant analysis program, depending on the application and maintenance objectives. These approaches commonly involve using either a conventional laboratory or on-site microlaboratory equipment. The advantage of the conventional laboratory approach is having a complete set of measuring equipment and dedicated expert technicians to operate and interpret results. Downsides include typically long turnaround times from sample collection to delivery of a quantitative report, possible sample contamination, and other mishandling issues. For at least these reasons onsite service engineers can rarely rely on laboratory reports to make real-time decisions.

Alternatively, technology has made it possible to have portable battery-powered lubricant analysis tools with capabilities comparable to equipment used in laboratories. Such device is disclosed in. U.S. Pat. No. 9,791,386 B2 to Henning et al. and assigned to Spectro Scientific, Inc. of Chelmsford, Mass. (see https://www.spectrosci.com/the-latest/press-relates/fieldlab-58-portable-fluid-analysis-system-from-spectro-scientific-boosts-performance-with-new-x-ray-fluorescence-xrf-engine/). The '386 patent is hereby incorporated by reference. The disclosed device integrates four analytical technologies, including X-Ray fluorescence (XRF) for elemental analysis, a filter particle qualifier (FPQ) pore blockage particle counter, an infrared (IR) spectrometer, and a kinematic viscometer (40° C.). Through its four manual operations, the device can generate test results in 5-7 minutes. Such devices typically weigh about 1.5 kg and require extensive training, if not expertise, to operate. Nonetheless, these mobile devices empower service engineers to make more informed decisions about machine and vehicle preventive maintenance.

Until the invention of the present application, these and other problems in the prior art went either unnoticed or unsolved by those skilled in the art. The present invention provides a system and method with remote hyperspectral sensing technology using an instrument weighing less than 1 kg. The system and method combine hyperspectral data processing and a Cloud-based element spectrum database to generate quantitative analysis in 3-5 seconds with Laboratory-comparable results to give service engineers more convenient and effective maintenance-based information from a diagnosis, while the instrument can be operated by a less skilled engineer with high throughput. Lubricant samples (less than 2 ml) can be repeatedly inspected, stored, and traced. The disclosed invention performs multiple functions with the associated device without sacrificing, portability, ease of use, and accuracy of results.

SUMMARY OF INVENTION

There is disclosed herein an improved system and scanner for analyzing lubricating oil samples which avoids the disadvantages of prior devices while affording additional structural and operating advantages.

Generally speaking, the system for analyzing fluid for contaminants comprises a fluid sample container for retaining a lubricating fluid sample, a hyperspectral scanner, a hyperspectral library comprised of data relating laboratory reflectance numbers for to an element content in a subject oil, and a server wirelessly connected to the scanner and having processing software to match sample reflectance numbers for each incremental band to laboratory reflectance numbers from the hyperspectral library. System characteristics include ease of operation, quick results, and improving precision as a result of self-learning.

The hyperspectral scanner comprises a light emitter for directing light into the lubricating fluid sample, wherein the directed light has wavelengths in the 400- 1000 nm range, a light receiver to receive reflected light from the lubricating fluid sample, and a photoelectric converter for converting incremental bands of the reflected light into sample reflectance numbers.

Further, disclosed is a method for quantitatively analyzing a lubricating, fluid for contaminants. Generally speaking, the method comprises taking a sample of a lubricating fluid to be analyzed, directing a light into the lubricating fluid sample, wherein the directed light has wavelengths in the 400-1000 nm range, receiving reflected light from the lubricating fluid sample, converting incremental bands of the reflected light into sample reflectance numbers, providing a hyperspectral library comprised of data relating; laboratory reflectance numbers to an element content in a subject oil, matching each sample reflectance number for each incremental band with a laboratory reflectance number from a hyperspectral library, and reporting the element content for each matched sample reflectance number.

Finally, a method for building a hyperspectral library for lubricating fluid analysis is also disclosed. The method comprises collecting a plurality of lubricating fluid samples representing different run-times on a specific machine, analyzing each of the plurality of lubricating fluid samples for quantified element content, scanning each of the plurality of lubricating fluid samples with a hyperspectral scanner to produce a hyperspectral image, measuring reflectance of each of the plurality of lubricating fluid samples at a plurality of intervals within the range of 400 to 1000 nm plotting the measured reflectance as a data point for each of the plurality of intervals to produce a curve, associating the quantified element content of each of the plurality of lubricating fluid samples with the corresponding curve, and storing each of the curves with the associated quantified element content in a database.

These and other aspects of the invention may be understood more readily from the following description and the appended drawings.

BRIEF DESCRIPTION OF THE DRAWINGS

For the purpose of facilitating an understanding of the subject matter sought to be protected, there are illustrated in the accompanying drawings, embodiments thereof, from an inspection of which, when considered in connection with the following description, the subject matter sought to be protected, its construction and operation, and many of its advantages should be readily understood and appreciated.

DETAILED DESCRIPTION OF A PREFERRED EMBODIMENT OF INVENTION

Figure 1:
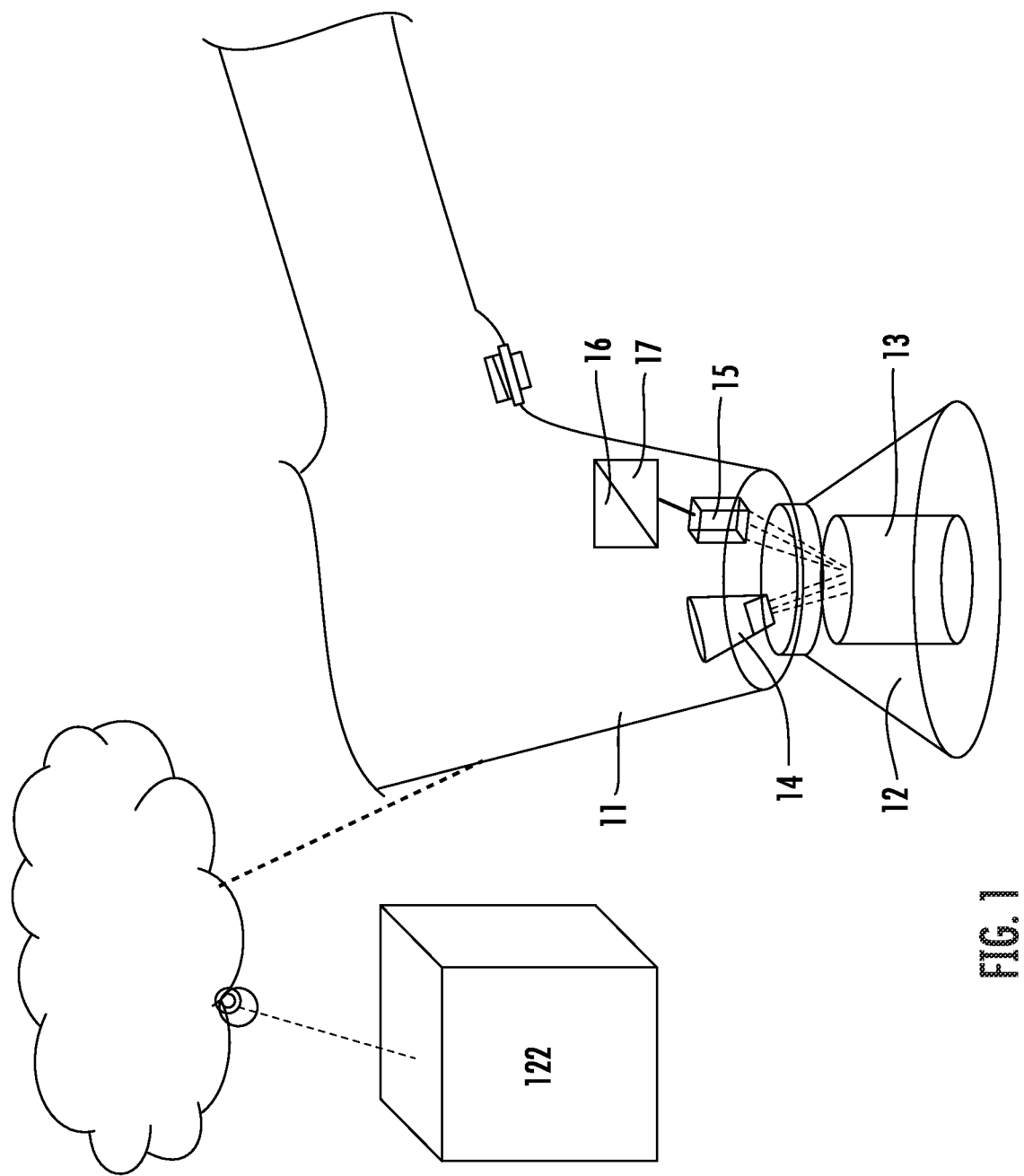
FIG. 1 illustrates an embodiment of a hyperspectral sensing instrument and its peripherals.

While this invention is susceptible of embodiments in many different forms, there is shown in the drawings and will herein be described in detail at least one preferred embodiment of the invention with the understanding that the present disclosure is to be considered as an exemplification of the principles of the invention and is not intended to Limit the broad aspect of the invention to any of the specific embodiments illustrated.

Referring to FIGS. 1-6, there is illustrated a system and method for remote hyperspectral sensing and analysis of fluid samples. The disclosed system includes a portable, battery-operated, remote, hyperspectral sensing instrument, generally indicated by the numeral 11. As shown, the instrument 11 comprises a light source (emitter) 14, a light detector (receiver) 15 and spectral splitter 16, and a photoelectric converter 17. The instrument 11 is connected to a data processing unit 120, via wireless transmission using the Internet and a Cloud-based server 111.

Using the portable instrument 11, the system can calibrate and match data by a hyperspectral model and output data corresponding to a composition of any material in a liquid sample (e.g., metal elements). The sample testing can be done onsite with results in a relatively short period of time. The output data can be formatted as a report providing diagnostic information, recommendations, and/or merely calling attention (i.e., alerts) to the sample and providing application scenarios.

The system is composed by the instrument 11 which connects to the Cloud-based server 122. The instrument consists of acquisition peripherals, hyperspectral acquisition, processing and transmission, and result display. The Cloud-based server 122 consists of an information platform, calibration and processing, hyperspectral model matching, application driven expert system, measure result and diagnosis.

In addition to the instrument 11, acquisition peripherals include equipment such as a sample container 13 with an NFC chip to hold about 1.6-2.0 ml lubricant oil sample and its unique electronic ID (UID), a black and white standard reflection board for calibration, an acquisition base (i.e., create a dark environment) to support the system during acquisition, and a lens' hood 12, The system registers the sample container UID in a database and binds the container with a point of inspection (engine or rotary equipment) where oil type is known through a QR code sweep gun (not shown The instrument 11 is able to connect the oil sample with the Cloud-based server 122 during test operation, so the right Hyperspectral Model can be used to match, and results can be transmitted to the instrument 11, and stored in the database.

The hood 12, as shown in FIG. 1, is used to make sure operation is consistent and independent from human involvement and keeps "light noise" low by keeping the light source as uniform for each acquisition as possible.

Figure 2:
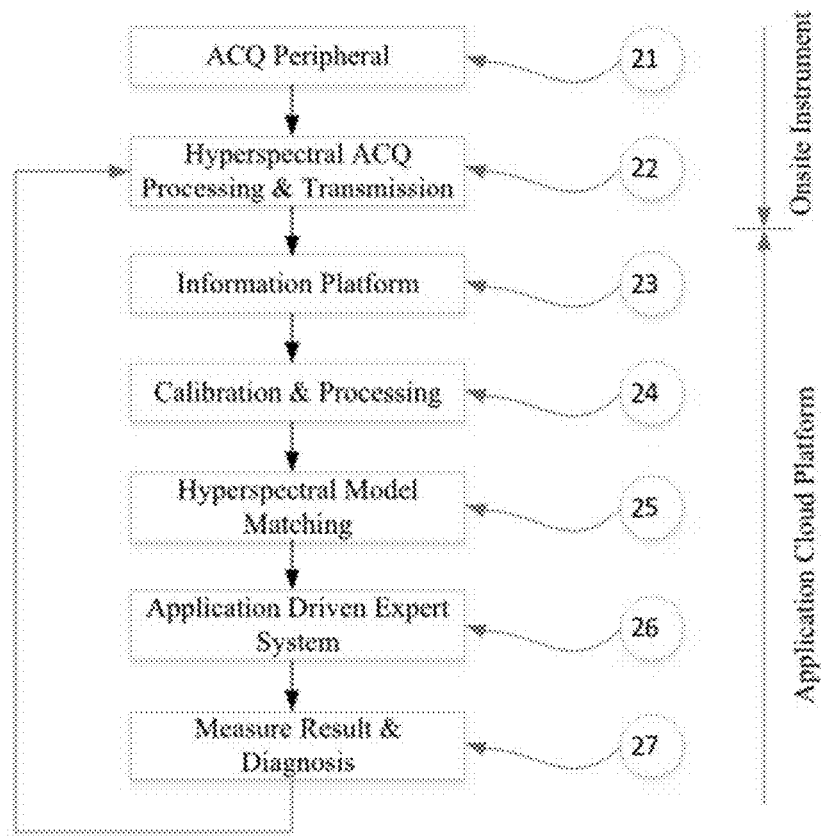
FIG. 2 is a process flowchart of an embodiment of the disclosed system.

With reference to FIG. 2, the following defines some terms and describes embodiments of specific components used in the disclosed system.

Acquisition Peripheral 21. This component provides equipment such as a sample container, with NFC chip to hold lubricant oil sample and its ID, a black and white standard reflection board for calibration, an acquisition base (dark environment) to support the instrument during acquisition, a lens' hood to make sure the system produces consistent acquisition data independent from every operation.

Hyperspectral Acquisition, Processing and Transmission 22. This process describes the functions provided by the instrument. For example, a. It preferably uses a halogen light source to produce a uniform and smooth emission line form hyper-spectrum with a characteristic wavelength (band) of 400-1000 nm;

b. It uses a detector to form an angle from the light source to maximum reflection acceptance;

c. It uses a hyperspectral splitter after the detector to segment acquired spectrum band width with 3 nm resolution into 200-300 intervals (bands);

d. It runs through a photoelectric converter in each individual band to generate reflection and DN values, respectively;

e. It combines results of all intervals, forms two data series with band intervals as horizontal axis, called "two curves";

f. it uses 4G to transmit the two curves to the dedicated the Cloud-based server; and g. It displays the element contents, element traced curve, and recommendation. information, received from the Cloud-based server.

Information Platform 23. This component responds to setup a connection channel between an instrument and the Claud-based server which facilitates an application driven platform dedicated for the end user.

Calibration and Processing 24. This component responds to measure the instrument and acquisition environment and compares to its initialization setting, use difference to generate compensation value for each band, applies them during each acquisition to offset the system errors and make sure the acquisition data consistent and stable.

Hyperspectral Model Matching Processing 25. This feature is comprised of two distinct procedures. First, the process is tasked with building a Hyperspectral Model based on a given number of oil samples with laboratory test results. A proprietary data processing method is used as well as a Hyperspectral Library to build the Hyperspectral Model (see detail illustrated in FIG. 4). Second, the process calculates the acquisition oil sample testing results through a Hyperspectral Model matching process. The proprietary data processing method and Hyperspectral Model are used to calculate the results (see detail illustrated in FIG. 5).

Application Driven Expert System 26. This component uses application domain knowledge applied to the test results and provides meaningful information to less skilled onsite users to obtain mission critical maintenance diagnosis and recommendation in seconds. It is based on data accumulation and lubricant oil information to reconstruct a new (or updated) Hyperspectral Model for precision improvement and measurement expansion.

Measure Results and Diagnosis 27. This component responds to store, display, and trace the results. It also provides data management and authorization for distribution.

As previously noted, the hyperspectral sensing instrument 11 produces a uniform and smooth emission line with a characteristic wavelength (band) of 400-1000 nm. The composition of any dissolved material, metal elements, in the lubricant oil sample will have a different reflectivity of light at different wavelengths (bands) between 400 and 1000 nm. The reflectivity is detected by the instrument. Each element can be represented by a reflection value and a digital number (DN), as a function of the different wavelength hands. The reflection value and DN are as follows:

$$\text{Reflection} = f_1(\text{band})$$

$$DN = f_2(\text{band})$$

The detector 15 on the instrument 11 forms an angle with the light source 14 to maximize reflection acceptance. A hyperspectral splitter 16 after the detector 15 is used to segment the acquired spectrum with about 3 nm resolution or band widths. As a result, the splitter 16 divides the spectrum into about 200 to 300 distinct bands. Each individual band runs through a photoelectric converter to generate the reflection and DN values. By plotting the results of all the individual bands, two curves are formed based on the formulas above: Using broadband cellular network (4G or greater), the two curves are transmitted to a dedicated Cloud-based server 122. To summarize the process of Hyperspectral acquisition above, each acquisition operation emits hyperspectral light to the substance, receives reflection spectrum, splits the spectrum into distinct bands, converts the reflectance into two numbers, generates two curves based on the two numbers at each band and broadcasts the two curves to the Cloud-based server for storage.

The information platform 23 indicated in FIG. 2 is the gate of the Cloud-based server 122. It communicates onsite with the instrument 11 and the processing units in the Cloud-based server. In addition to the instrument ID lubricant oil sample container ID—in which the type of lubricant oil, oil sample collection time, instrument internal temperature, etc., can be sorted from the system—and hyperspectral acquisition data (i.e., the two curves) are transmitted to the Cloud-based server. The Information platform 23 uses the instrument ID to verify attribution and legitimacy and set communication channel for return testing results. The information platform 23 also plays a connection role and is able to expend itself to handle hundreds of instruments to conduct testing at the same time.

The calibration and processing 24 of FIG. 2 is another component in the Cloud-based server 122. Calibration and processing 24 is responsible for removing system error and acquisition setting deviation due to any environment inconsistency from uploaded acquisition data (two curves). In order to have a hyperspectral model to analyze, match acquisition data and provide test results independent from instruments and acquisition environments, each instrument 10 may carry characteristic curves (for entire 600 nm bandwidth). The characteristic curve for each device should be measured by a standard optical plate in an environment based on the peripherals accompanying the instrument prior to release to user. Periodically, users of the instrument should conduct a similar process with the same setting (not necessarily exactly conditions) to obtain calibration curves. The difference between the characteristics curve and the calibration curve for each instrument is used to calculate a compensation curve to apply to each acquisition data point to correct the deviation introduced by instrument and acquisition environment, as well as that caused by worn out and inconsistent operation.

Preferably, calibration is conducted periodically by user applying the necessary calibration procedures to generate calibration curves according to the application. However, the role of calculating compensation curves and applying correction to acquisition data is that of the calibration and processing component in the Cloud-based server 122.

Hyperspectral Model Matching is another component of the system 11 which is part of the Cloud-based server 122. This component takes acquisition data from a lubricant oil sample as input, after calibration of the two curves, then outputs quantitative analysis elements for the lubricant oil sample, such as iron (Fe) and copper (Cu) content (in mg/L). The hyperspectral model matching component consists of a Hyperspectral Library in which a collection of element spectrum is placed, such as spectral extraction, spectral discrimination, and spectrum matching processing components.

The Hyperspectral Model Matching has two tasks. The first task, based on a limited number of laboratory oil sample test results, which statistically cover entire subject lubricant application life cycle distribution and acquisition data of these oil samples, is to build a Hyperspectral Model. The second task, based on the Hyperspectral Model, is to calculate the element from input acquisition data (two curves) in a lubricant oil sample within its distribution. This is discussed further below.

Figure 5:
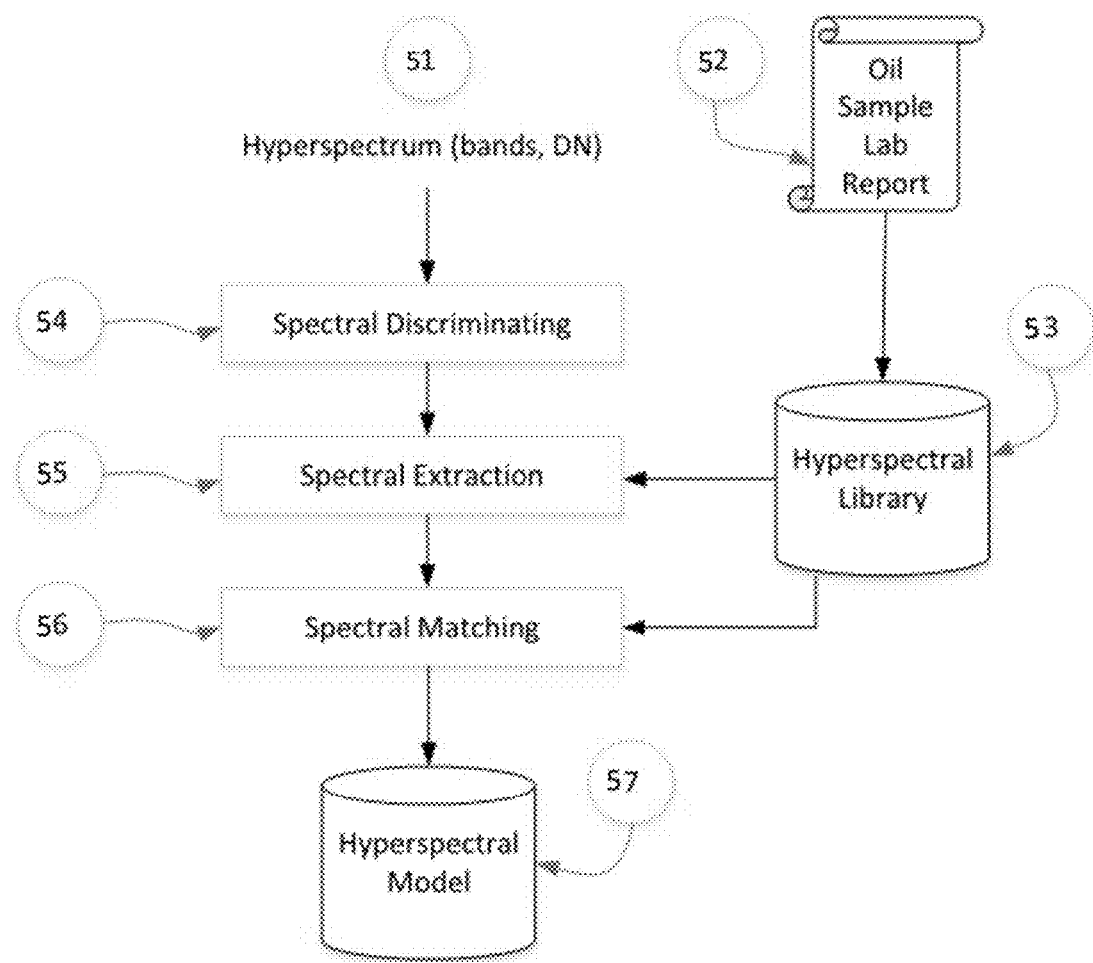
FIG. 5 is the Processing Procedures to Calculate the Test Results.

In order for the system to quantitatively measure elemental contents in the lubricant oil sample, it needs to build Hyperspectral Model based on the same type of subject lubricant oil. FIG. 5 is a flowchart illustrating how to build a proper Hyperspectral Model. Building a Hyperspectral Model requires a certain number of oil samples distributed throughout the entire lifecycle of the specific lubricant. A preferred embodiment of the process for building a hyperspectral model is as follows:

1. Obtain laboratory test results of a given number of oil samples;
2. Use disclosed system to acquire data points for oil sample to plot its two curves (see FIG. 5, 51).
3. Input laboratory test report of the same oil sample into the system (see FIG. 5, 52);
4. The laboratory result of the oil sample determines which elements and other contents the system will measure. (see FIG. 53);
5. For all elements, two curves represent reflection and DN values for entire bandwidth of 400-1000 nm, or approximately 200-300 intervals/data points, In order to discriminate, identify, or detect target of interest, a spectral derivative feature coding is applied to hyperspectral signature discrimination and data classification (see FIG. 5, 54);

6. For specific elements, only reflection and DN values of subset intervals are needed. The computational intelligence method for band selection, as known by those in the art, combined with the specific element-defined parameters from the Hyperspectral. Library after inputting laboratory results of oil samples, will yield better extraction results (see FIG. 5, 55);
7. The element corresponding to bands from Hyperspectral Library is used to match reflection and DN values of bands. The quantitative content of the element from the laboratory results is paired to the characteristic of reflection and DN values (see FIG. 5, 56);
8. The paired result corresponding to the laboratory test element content, reflection and DN values of the bands, are stored, which represent the element content of the oil sample in the Hyperspectral Model (see FIG. 5, 57);
9. The process of steps 6-8 is repeated until all elements in the laboratory test result in the oil sample are counted; and
10. The process is then repeated, beginning with step 2 above, until all oil samples used to build Hyperspectral Model are counted.

The Hyperspectral Model 57 indicates the relationship between each element content corresponding to reflection and DN values of bands for a type of lubricant. Experimental results suggest that Hyperspectral Model 57 can hold multiple types of lubricants independent from the engine or rotating equipment to which it is applied.

It is easy to understand that a Hyperspectral Model 57 binds a type of lubricant or an application scenario. The Hyperspectral Model 57 can be assigned which can be associated with the lubricant oil sample container ID. In another words, the instrument obtains the lubricant oil sample container ID through near field communication (NFC) protocol, the system is able to pair the Hyperspectral Model to measure its acquisition data (two curves).

Figure 3:
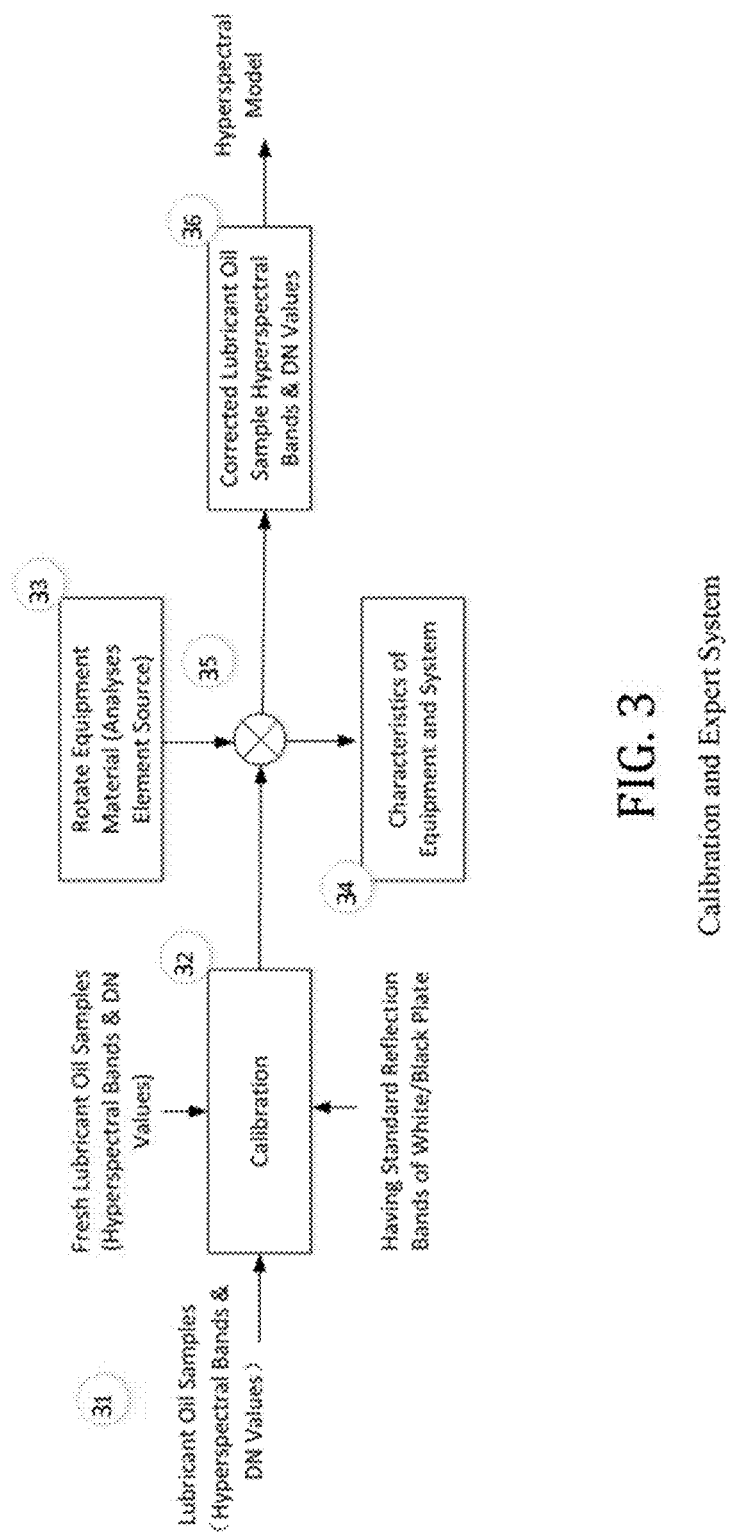
FIG. 3 is a system diagram of an embodiment of system calibration and an application-driven expert system.

FIG. 3 is the system diagram of calibration and Expert System, it includes two procedures. One is for calibration (see FIG. 3, 32) and the other is for an application driven expert system (see FIGS. 3, 33, 34 and 36), Both make sure to provide quality and better resolution acquisition data (two curves) for the Hyperspectral Model matching processing.

Acquisition inputs include dedicated data for calibration. For example, fresh lubricant oil sample reflection and DN values (i.e., clean oil before use) based on bands, and standard black and white optical plate reflection and DN values can be used as baselines (see FIG. 3, 32). That is, the fresh lubricant oil sample reflection and DN values can actually provide a way to remove background noise from normal acquisition data (i.e., reflection and DN values) through a subtraction corresponding to each band. This calibration enhances metal dust elements introduced in actual oil samples during the normal operation of lubricating engines or rotary equipment. Likewise, the standard black and white optical plates produce known reflection and DN values during initialization.

The same procedure can be used to measure plates at "power on" for the instrument prior to each testing. Any differences recorded over time will reflect degradation of the instrument. However, the system can use the measured difference to calculate a compensation value for the reflection and DN values of the acquisition data in real time. Accordingly, calibration is a processing unit of the system to measure and calculate the compensation needed to obtain correct and consistent reflection and DN values for each band.

Understanding measurement equipment and determining the elements in an oil sample to measure will help the Hyperspectral Model matching procedure. For example, it can help in the diagnosing of the subject engine or equipment runtime condition by knowing characteristics of the engine, equipment, or system (see FIG. 3, 34). It also helps the system to interpolate the acquisition data. Using the disclosed process will present acquisition data, include reflection and DN values, after the necessary correction is applied. As a result, it will minimize the dependence of the acquisition data on different instruments, environment, and the operator.

Figure 4:
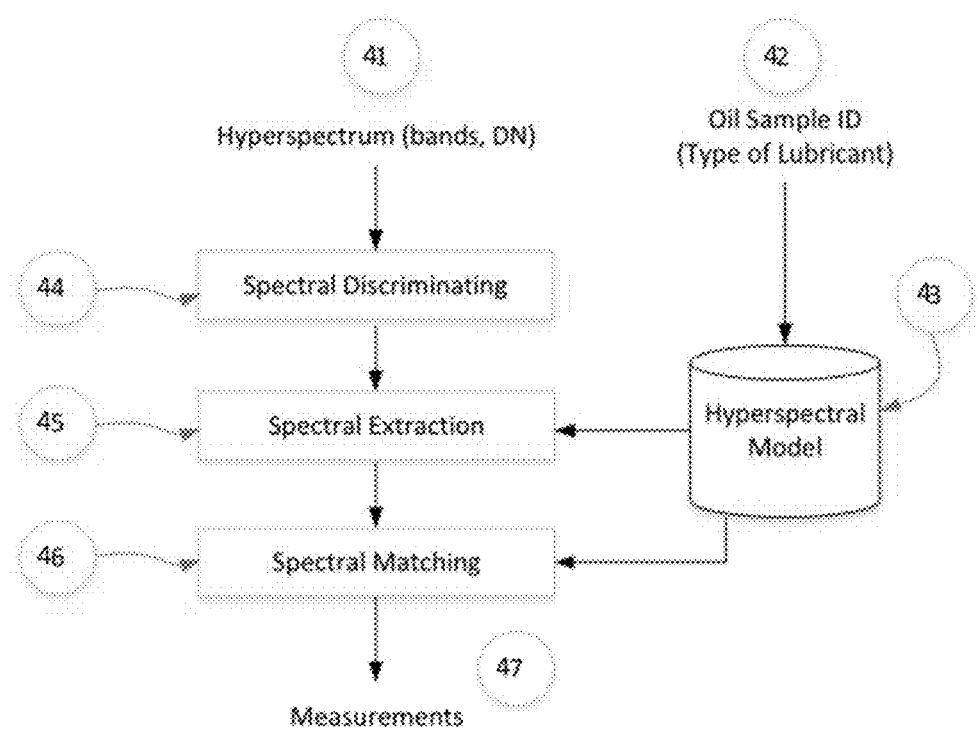
FIG. 4 is a flow chart illustrating a processing procedure for building hyperspectral models.

FIG. 4 is a flowchart illustrating how to measure the element content from the acquisition data acquired from a lubricant oil sample in the field. The flowchart is explained in more detail below:
1. The instrument 11 is used to read the oil sample container ID and acquires the oil sample to get its two curves (see FIG. 4, 41);
2. The system matches the Hyperspectral Model with the oil sample container ID (see FIG. 4, 42);
3. For all elements, two curves represent reflection and DN value of entire bandwidth of 400-1000 nm, ranging between 200-300 intervals/data points. In order to discriminate, identify, or detect target of interest, a spectral derivative feature coding is applied to hyperspectral signature discrimination and data classification (see FIG. 4, 44);
4. For a specific element, the system only needs reflection and DN values of a subset of intervals. As previously noted, the computational intelligence method for band selection combined with element-defined parameters from Hyperspectral Model 68 will yield better extraction results (see FIG. 4, 45);
5. The element corresponding to bands from the Hyperspectral Model 43 are then used to match reflection and DN values of bands, locate "neighbors" of reflection and DN values of bands, apply bandwidth spatial convolution to interpolate quantitative content of the subject element from the Hyperspectral Model (see FIG. 4, 46);
6. The measured element content of the oil sample is then stored in a system database with an index of the oil sample container ID (see FIG. 4, 47). The stored data may be used to associate a point in test or engine service records with a time label; and
7. The process is repeated from step 3 above until all elements in the oil sample are counted.

With the procedures disclosed above, comparable laboratory test results of a lubricant oil sample can be obtained using the disclosed hyperspectral sensing instrument 10 and system, in as little as a few seconds. The instrument 11 is lightweight, preferably handheld, compact enough to fit any specific application scenario, and easy enough to operate by maintenance personnel that it does not require a dedicated technician.

The instrument 11 provides at least two opportunities for better maintenance and service, including 1) providing a direct diagnosis of the "health status" of equipment as a clinic physical exam report rather than merely providing element contents in the oil sample that would require dedicated personnel to interpret, and 2) keeping the instrument independent from the specific application scenario and the Hyperspectral Model independent from the instrument, which allows the Hyperspectral Model to leverage big data self-learning and improve the precision and sample interval of the lubricant. An Application Driven Expert System (see FIG. 2, 26) in the Cloud-based server is designed to satisfy these two opportunities and more.

The Application Driven Expert (ADE) System is a self-sufficient container (i.e., as in software terminology, not a physical container), automatically deployed by the system based on an application that can run in the Cloud-based server. The ADE System offers an end user access to the system. It corresponds to at least one instrument by binding its ID. It provides an application scenario to input the way a skilled technician and/or scientist using test results of an oil sample to diagnosis or analysis the "health condition" of a machine, wind turbine, vehicle, ship or jet engine, etc., and to make a recommendation based on the analysis. For example, a certain level of iron (Fe) content in a lubricant oil sample from a wind turbine would mean the wind turbine paddle bearings are worn out. As a result, a maintenance procedure may be recommended. Such a threshold level can be set into the "container" to trigger an alert. Since the instrument 10 binds to the application (via ID), it can be operated by a less skilled worker on site to obtain the same diagnosis and recommendation in seconds.

FIG. 5 is the Processing Procedures to Calculate the Test Results. It includes the following steps:
1. Obtain oil sample container ID from the instrument to determine the corresponding Hyperspectral Model to use (through UID).
2. Use the instrument to acquire the reflection and DN values with entire bandwidth from the oil sample as input.
3. Hyperspectral Model is the data base unit in which the spectrum including reflection and DN values of element contents corresponding to reflection and DN values of entire bandwidth obtained from a set of oil sample from a type of lubricant are stored.
4. It is a standard data processing utilities to enhance acquisition data (step 2 above).
5. It is a standard data processing utilities to extract a subset of bands for specific element to be measured according to Hyperspectral Model reference.
6. It is the procedure to use Hyperspectral Model contents according to the matching mechanism to interpolate the characteristics of the reflection and DN values of input oil samples.
7. The corresponding results (element content) are stored in the data base indexed by the oil sample (container) ID with oil sample acquisition time label attached.

Figure 6:
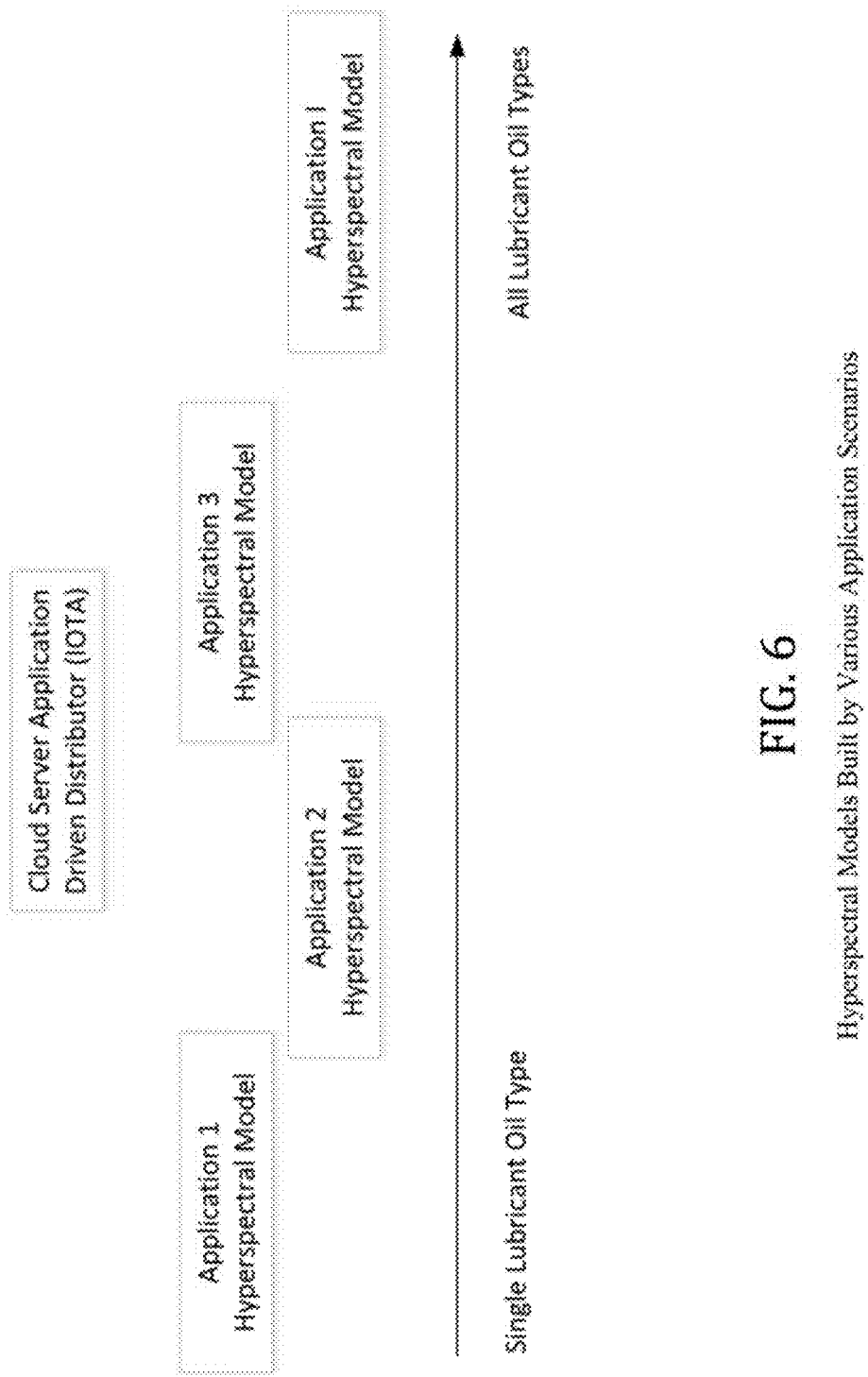
FIG. 6 illustrates a number of hyperspectral models built by various application scenarios in the system.

FIG. 6 illustrates a number of hyperspectral models built by various application scenarios in the system. When the same type of lubricant oil is taken from the same or different engine or equipment scenarios, the system is able to reconstruct the existing hyperspectral model for that lubricant oil to create a new one with better precision without user interruption for a specific scenario. This is referred to as "self-learning" and greatly improves precision of the instrument.

Based on various applications, the system can deploy appropriate self-sufficient containers. Each software container corresponds to an application scenario, while each application corresponds to a Hyperspectral Model. The more application scenarios deployed, the greater the number of Hyperspectral Models in the system to be built (see FIG. 6).

In a situation where there are different applications for the same type of lubricant, then multiple Hyperspectral Models create overlap in data and provide more detection area for the lubricant. The greater data allows the system to update/reconstruct the Hyperspectral Models, whereby precision becomes much better for the overlapping area, and the detection range may even increase.

For example, using a wind turbine analysis for iron (Fe) content, two Hyperspectral Models (e.g., different customers) might correspond to 2 megawatt (MW) and 4 MW wind turbine applications. Both turbines use the same lubricant in the paddle bearing. Iron (Fe) content ranges between 0-1300 mg/kg in the Hyperspectral Model of the 2 MW turbine, while the Fe content range is between 300-1800 mg/kg in the Hyperspectral Model of the 4 MW turbine, With data from both models, the Hyperspectral Models of both the 2 MW and 4 MW wind turbines can be reconstructed/updated by the system. This process increases precision as a result of the increase in sample size. It also expands the analysis range for the wind turbines when the iron (Fe) content increases beyond the original modeling area. Iron as well as other materials, can be quantitatively measured and exceeding thresholds can trigger an alert when anything potentially catastrophic happens in the bearings. As a result, the instrument improves its measure area and precision by self-learning.

The system includes a database which stores data, including the measure results, diagnosis, and any recommendations according to the acquisition time stamp. It is herein referred to as the "Measure Result & Diagnosis" component in the Cloud-based server 122 (see FIG. 2). This component is the foundation of the sample analysis methods, trends of Lubricant changes by run time, data display corresponding to bands, time, application mark, and recommendations. The results, including data display, can be pushed to the remote instrument on site through the information Platform (see FIG. 2, 23).

The matter set forth in the foregoing description and accompanying drawings is offered by way of illustration only and not as a limitation. While particular embodiments have been shown and described, it will be apparent to those skilled in the art that changes and modifications may be made without departing from the broader aspects of applicants' contribution. The actual scope of the protection sought is intended to be defined in the following claims when viewed in their proper perspective based on the prior art.

What is claimed is:
1. A system for analyzing fluid for contaminants, the system comprising:
   a fluid sample container for retaining a lubricating fluid sample;
   an integrated, portable hyperspectral scanner comprising:
      a light emitter for directing light into the lubricating fluid sample, wherein the directed light has wavelengths in the 400-1000 nm range;
      a light receiver to receive reflected light from the lubricating fluid sample; and
      a photoelectric converter for converting incremental bands of the reflected light into sample numbers;
   a hyperspectral library comprised of data relating laboratory derived numbers for an element content in a subject oil; and
   a server wirelessly connected to the scanner and having processing software to match sample numbers for each incremental band to laboratory derived numbers from the hyperspectral library.
2. The system of claim 1, wherein the laboratory derived numbers are at least one of either reflectance numbers or digital numbers.
3. The system of claim 2, wherein the sample numbers are at least one of either reflectance numbers or digital numbers.
4. The system of claim 1, wherein the data relating laboratory derived numbers for an element content in a subject oil comprises a hyperspectral model.

5. The system of claim 4, wherein the server has integrated components comprising an information platform, a calibration and processing feature, a hyperspectral model matching feature, an application driven expert system, and a measure result and diagnosis feature.

6. The system of claim 5, wherein the information platform provides a connection channel between the scanner and the server.

7. The method of claim 6, wherein each of the plurality of intervals is approximately 3 nm.

8. The system of claim 1, wherein the fluid sample container comprises a near-field communication (NFC) chip and a unique identification stored on the NFC chip which can be remotely read by the system.

9. The system of claim 5, wherein the information platform comprises an application dedicated to a user of the scanner.

10. The system of claim 5, wherein the calibration and processing feature comprises programming which:
measures parameters of the scanner and acquisition environment;
compares the measured parameters to initial settings;
generates a compensation value for each band;
applies compensation value for each band during acquisition to offset system errors.

11. The system of claim 5, further comprising a self-learning feature wherein new data added to the hyperspectral library is automatically used to update the hyperspectral model.

12. A hyperspectral scanning instrument comprising:
a light emitter for directing light into a lubricating fluid sample, wherein the directed light has wavelengths in the 400-1000 nm range;
a light receiver to receive reflected light from the lubricating fluid sample;
a photoelectric converter for converting incremental bands of the reflected light into sample reflectance numbers; and
a wireless transceiver for communicating to a server, the server comprising:
a hyperspectral library comprised of data relating laboratory reflectance numbers to an element content in a subject oil; and
processing software to match sample reflectance numbers for each incremental band to laboratory reflectance numbers from the hyperspectral library.

13. The hyperspectral scanning instrument of claim 12, wherein the instrument is portable.

14. The hyperspectral scanning instrument of claim 12, wherein the instrument comprises the ability to self-learn.

15. The hyperspectral scanning instrument of claim 14, wherein the data relating laboratory reflectance numbers for an element content in a subject oil comprises a hyperspectral model.

16. The hyperspectral scanning instrument of claim 15, wherein the ability to self-learn comprises software which takes new data added to the hyperspectral library to automatically update the hyperspectral model.

17. A method for quantitatively analyzing a lubricating fluid for contaminants, the method comprising:
taking a sample of a lubricating fluid to be analyzed;
directing a light into the lubricating fluid sample, wherein the directed light has wavelengths in the 400-1000 nm range;
receiving reflected light from the lubricating fluid sample;
converting incremental bands of the reflected light into sample reflectance numbers;
providing a hyperspectral library comprised of data relating laboratory reflectance numbers to an element content in a subject oil;
matching each sample reflectance number for each incremental band with a laboratory reflectance number from a hyperspectral library; and
reporting the element content for each matched sample reflectance number.

18. The method of claim 16, further comprising using a hyperspectral scanner to direct light, receive reflected light and convert to sample reflectance numbers.

19. The method of claim 17, further comprising calibrating the hyperspectral scanner.

20. The method of claim 18, wherein calibrating comprises:
measuring parameters of the scanner and acquisition environment;
comparing the measured parameters to initial settings;
generating a compensation value for each band;
applying the compensation value for each band during acquisition to offset system errors.

* * * * *